US010517296B2

(12) United States Patent
Yamada

(10) Patent No.: US 10,517,296 B2
(45) **Date of Patent: *Dec. 31, 2019**

(54) INSECT PEST CONTROL MATERIAL

(71) Applicant: Innovative Vector Control Consortium, Liverpool, Merseyside (GB)

(72) Inventor: Noriko Yamada, Takarazuka (JP)

(73) Assignee: INNOVATIVE VECTOR CONTROL CONSORTIUM, Liverpool, Merseyside (GB)

( * ) Notice: Subject to any disclaimer, the term of this patent is extended or adjusted under 35 U.S.C. 154(b) by 5 days.

This patent is subject to a terminal disclaimer.

(21) Appl. No.: 15/761,784

(22) PCT Filed: Sep. 23, 2016

(86) PCT No.: PCT/JP2016/077943
§ 371 (c)(1),
(2) Date: Mar. 20, 2018

(87) PCT Pub. No.: WO2017/051841
PCT Pub. Date: Mar. 30, 2017

(65) Prior Publication Data

US 2018/0263241 A1 Sep. 20, 2018

(30) Foreign Application Priority Data

Sep. 25, 2015 (JP) ................................ 2015-187870
Jul. 11, 2016 (JP) ................................ 2016-136595

(51) Int. Cl.
*A01N 43/54* (2006.01)
*A01N 25/10* (2006.01)
*A01N 25/34* (2006.01)

(52) U.S. Cl.
CPC ............ *A01N 43/54* (2013.01); *A01N 25/10* (2013.01); *A01N 25/34* (2013.01)

(58) Field of Classification Search
CPC ........ A01N 43/54; A01N 25/34; A01N 25/10; A47C 29/006; Y02A 50/372
See application file for complete search history.

(56) References Cited

U.S. PATENT DOCUMENTS

2005/0132500 A1 6/2005 Karl et al.

FOREIGN PATENT DOCUMENTS

| | | | |
|---|---|---|---|
| JP | H06-502864 | A | 3/1994 |
| JP | H07-258223 | A | 10/1995 |
| JP | 2007-524773 | A | 8/2007 |
| JP | 2012-001533 | A | 1/2012 |
| WO | WO-92/08704 | A1 | 5/1992 |
| WO | WO-2005/064072 | A2 | 7/2005 |

OTHER PUBLICATIONS

International Search Report with English translation and Written Opinion issued in International Application No. PCT/JP2016/077943 dated Nov. 22, 2016.

*Primary Examiner* — Robert S Cabral
(74) *Attorney, Agent, or Firm* — Foley & Lardner LLP

(57) ABSTRACT

The present invention provides: an insect pest control material obtained by causing 5-chloro-4-ethyl-6-[2-(4-trifluoromethylphenyl)ethylamino]pyrimidine to be held on the surface of a base material comprising polyester multifilaments; and a pest control method provided with a step in which the insect pest control material is placed in a pest habitat.

6 Claims, No Drawings

INSECT PEST CONTROL MATERIAL

TECHNICAL FIELD

Related Applications

The present application claims priority under 37 U.S.C. § 371 to International Patent Application No. PCT/JP2016/077943, filed Sep. 23, 2016, which claims priority to and the benefit of Japanese Patent Application Nos. 2015-187870 filed on Sep. 25, 2015 and 2016-136595 filed on Jul. 11, 2016. The contents of these applications are hereby incorporated by reference in their entireties.

The present invention relates to a pest control material.

BACKGROUND ART

Various pest control materials such as textile, fabric, and net products which are coated with pyrethroid insecticides on the surface is widely used to control pests such as mosquito (see Patent Document 1). However, the materials do not necessarily have sufficient performance, and it has been thus desired to provide a pest control material having an excellent control effect against pests.

CITATION LIST

Patent Document

Patent Document 1: WO 2005/064072 pamphlet

SUMMARY OF THE INVENTION

Problems to be Solved by Invention

An object of the present invention is to provide a pest control material having an excellent control effect against pests.

Means to Solve Problems

The present inventor has intensively studied to achieve the object and, as a result, found out that a pest control material comprising 5-chloro-4-ethyl-6-[2-(4-trifluoromethylphenyl)ethylamino]pyrimidine as an insecticidal ingredient on a surface of a base material composed of a multifilament made of polyester can bring in an excellent pest control efficacy, and thus the inventor achieved the present invention. That is, the present invention is as follows:

[1] A pest control material which is formed by retaining 5-chloro-4-ethyl-6-[2-(4-trifluoromethylphenyl)ethylamino]pyrimidine on a surface of a base material composed of a multifilament made of polyester.

[2] The pest control material according to [1], wherein the material is in a net form.

[3] The pest control material according to [1], wherein the material is in a mosquito bed net form.

[4] The pest control material according to any one of [1] to [3], wherein the content of 5-chloro-4-ethyl-6-[2-(4-trifluoromethylphenyl)ethylamino]pyrimidine is 0.1 to 10% by mass relative to a total amount of the pest control material.

[5] The pest control material according to any one of [1] to [4], which is further equipped with an inactive support material.

[6] A method for controlling pests comprising placing the pest control material according to any one of [1] to [5], in habitat of the pests.

The present invention can provide a pest control material having an excellent control effect against pests.

EMBODIMENT FOR CARRYING OUT THE INVENTION

The pest control material of the present invention (hereinafter, referred to as "the present pest control material") is formed by retaining 5-chloro-4-ethyl-6-[2-(4-trifluoromethylphenyl)ethylamino]pyrimidine on a surface of a base material composed of a multifilament made of polyester according to any process such as immersing, spreading and coating.

A multifilament made of polyester is prepared as a piece of fiber by twisting a plurality of filaments such as long-fibers, in which the filaments are produced by using polyester as a main raw material and optionally adding one or more of preservatives, stabilizers, agents having UV protecting properties, fluorescent whitening agents, spreading agents, anti-migrating agents, foam-forming agents, wetting agents, anti-soiling agents, thickeners, other biocides, plasticizers, adhesive agents, aromatic agents, pigments, or dyes.

A method for preparing the multifilament is described as follows, but is not limited thereto.

First, many yarns discharged from the fiber spinning nozzle are cooled by passing them through a cooling zone. This cooling may be carried out to such an extent that the yarns are not fusion-bonded to each other. After the cooling, an oil agent is applied to the yarns with an oiling roller. After rolling up the yarns or at a subsequent stretching step, the yarns are twisted (drafting) and are collected.

A thickness of the filament is preferably 1 to 25 denier(s). The thickness of 50 to 300 deniers is preferred when the filament is used as a multifilament, but the thickness can be optionally selected depending on its use.

In the present invention, the multifilament made of polyester may be directly used as a base material. Further, the multifilament made of polyester may be used as a net-formed base material, which is produced by twisting the multifilament made of polyester to a bobbin and then optionally knitting, weaving, and heat-fusing according to known methods. In addition, the multifilament made of polyester can be used as a net form by drawing up the pest control material which is formed by retaining 5-chloro-4-ethyl-6-[2-(4-trifluoromethylphenyl)ethylamino]pyrimidine on a surface of a multifilament made of polyester according to the above-mentioned process. A mesh size of the present pest control material in the net form (the size of space between multifilaments, i.e., hole size) is preferably 1 to mm in view of controlling pests, in particular, mosquitoes.

5-Chloro-4-ethyl-6-[2-(4-trifluoromethylphenyl)ethylamino]pyrimidine used in the present invention (hereinafter, referred to as "the present compound") can be prepared, for example, by a method described in Preparation Example 1 herein.

A content of the present compound is preferably 0.1 to 10% by mass, more preferably 0.1 to 4% by mass relative to a total amount of the present pest control material.

For example, the process for immersing and spreading a base material composed of a multifilament made of polyester can comprise dissolving or dispersing the present compound in one or more of suitable solvent(s) so as to achieve a desirable concentration, and then retaining the obtained solution or dispersion into a base material according to a letterpress printing method using a letterpress rotary press, copperplate rotary press, or resin plate rotary press, a photogravure printing method using a gravure printer, rotogravure printer, or engraving intaglio printer, an offset printing method using an offset printer, a lithography using a type lithographic printer, silkscreen, drum screen printer, or screen printing machine, a dipping method using a dipping machine, a spraying method using a sprayer, electrostatic spraying method using an electrostatic sprayer, etc., and optionally applying any process such as drying, heating and slitting.

In addition, the coating process can comprise dissolving or dispersing the present compound in one or more of suitable solvent(s), incorporating one or more of surfactant(s) and/or dispersant(s) to the obtained solution or dispersion to prepare a dispersion, further adding one or more binder(s) in the dispersion, and then coating a base material using a coating machine such as roll coater, blade coater, air-knife coater, cast coater and knife coater, and optionally applying any process such as drying, heating and slitting.

The solvent used in the immersing, spreading, or coating includes, for example, water, alcohols such as methanol, ethanol, isopropyl alcohol, butanol, hexanol, benzyl alcohol, ethylene glycol, propylene glycol and phenoxyethanol, ketones such as acetone, methyl ethyl ketone and cyclohexanone, aromatic hydrocarbons such as toluene, xylene, ethylbenzene, dodecylbenzene, phenylxylylethane and methylnaphthalene, aliphatic hydrocarbons such as hexane, cyclohexane, kerosene and light oil, esters such as ethyl acetate, butyl acetate, isopropyl mylistate, ethyl oleate, diisopropyl adipate, diisobutyl adipate and propyleneglycol monomethyl ether acetate, nitriles such as acetonitrile and isobutyronitrile, ethers such as diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether and 3-methoxy-3-methyl-1-butanol, acid amides such as N,N-dimethylformamide and N,N-dimethylacetamide, halogenated hydrocarbons such as dichloromethane, trichloroethane and tetrachlorocarbon, sulfoxides such as dimethylsulfoxide, propylene carbonate, and vegetable oils such as soybean oil and cottonseed oil, but are not limited thereto.

The surfactant used in the coating can include, for example, nonionic surfactants, e.g., polyoxyethylene alkyl ether, polyoxyethylene alkylaryl ether, polyoxyethylene lanolin alcohol, polyoxyethylene alkylphenol formalin condensate, polyoxyethylene sorbitan fatty acid ester, polyoxyethylene glyceryl monofatty acid ester, polyoxypropylene glycol monofatty acid ester, polyoxyethylene sorbitol fatty acid ester, polyoxyethylene castor oil derivative, polyoxyethylene fatty acid ester, higher fatty acid glycerol ester, sorbitan fatty acid ester, sucrose fatty acid ester, polyoxyethylene-polyoxypropylene copolymer, polyoxyethylene fatty acid amide, alkylolamide, polyoxyethylene alkylamine, etc.; cationic surfactants, e.g., alkylamine hydrochloride such as dodecylamine hydrochloride, alkyl quaternary ammonium salt, alkyl trimethyl ammonium salt such as dodecyl trimethyl ammonium salt, alkyl dimethyl benzyl ammonium salt, alkyl pyridinium salt, alkyl isoquinolinium salt, dialkyl morpholinium salt, benzethonium chloride, polyalkyl vinyl pyridinium salt, etc.; anionic surfactants, e.g., fatty acid sodium such as sodium palmitate, ether carboxylic acid sodium such as polyoxyethylene lauryl ether carboxylic acid sodium, amino acid condensate of higher fatty acid such as sodium lauroylsarcosine and sodium N-lauroyl glutamate, higher alkyl sulfonate salt, higher fatty acid ester sulfonate salt such as laurate sulfonate salt, dialkyl sulfosuccinate salt such as dioctyl sulfosuccinate salt, higher fatty acid amide sulfonate such as oleic acid amide sulfonate salt, alkylaryl sulfonate salt such as dodecyl benzene sulfonate salt and diisopropyl naphthalene sulfonate salt, formalin condensate of alkylaryl sulfonate salt, higher alcohol sulfate salt such as pentadecane-2-sulfate, polyoxyethylene alkyl ether sulfate salt such as sodium polyoxyethylene dodecyl ether sulfate salt, polyoxyethylene alkyl phosphate such as dipolyoxyethylene dodecyl ether phosphate, styrene-maleic acid copolymer, alkylvinyl ether-maleic acid copolymer, etc.; and ampholytic surfactants, e.g., N-lauryl alanin, N,N,N-trimethyl aminopropionate, N,N,N-trihydroxyethyl aminopropionate, N-hexyl-N,N-dimethyl aminoacetate, and 1-(2-carboxyethyl)pyridinium betaine, and lecithin, etc., and they can be used alone or in combination with two or more of the surfactants.

The dispersant used in the coating includes water-soluble polymer dispersants such as water-soluble natural polymer dispersants, water-soluble semi-synthetic polymer dispersants and water-soluble synthetic polymer dispersants, in particular, the water-soluble natural polymer dispersants include, for example, sodium alginate, gum arabic, guar gum, and xanthan gum, the water-soluble semi-synthetic polymer dispersants include, for example, cellulose-based dispersant such as carboxymethyl cellulose salt, the water-soluble synthetic polymer dispersants include, for example, polyvinyl alcohol and polyvinyl pyrrolidone. The water-soluble synthetic polymer dispersants are commercially available, and the polyvinyl alcohol includes GOHSENOL GL-03 (Nippon Synthetic Chemical Industry, Co., Ltd.), GOHSENOL GL-05 (Nippon Synthetic Chemical Industry, Co., Ltd.), and KURARY POVAL PVA-224 (KURARAY CO., LTD.), the carboxymethyl cellulose salt includes CELLOGEN 6A (DKS Co. Ltd.), CELLOGEN 7A (DKS Co. Ltd.), CMC DAICEL 1110 (Daicel Chemical Industries, Ltd.), and CMC DAICEL 1210 (Daicel Chemical Industries, Ltd.), the xanthan gum includes KELZAN (Sansho Co., Ltd.), and RHODOPOL 23 (Rhodia Nicca, Ltd.), and the polyol derivative includes AGRISOL FL-104FA (Kao Corporation), etc. In addition, the water-soluble polymer dispersants can be typically contained at a rate of about 0.1 to 5 wt %, preferably about 0.1 to 3 wt % to a total amount of an aqueous solution of the dispersants.

The binder used in the coating includes, for example, inorganic binders, natural organic binders, semisynthetic binders, synthetic resin binders, and wax, but is not limited thereto. The inorganic binders include bentonite, montmorillonite, water glass, and colloidal silica, etc. The natural organic binders include starch, dextrin, casein, gelatin, glue, agar, gum arabic, cornstarch, natural rubber, and pulp liquid, etc. The semisynthetic binders include cellulose-based binders such as carboxymethyl cellulose, carboxymethyl cellulose sodium salt, hydroxypropyl methyl cellulose, nitrocellulose, cellulose acetate, methylcellulose, ethylcellulose and hydroxypropyl cellulose, and lignin-based binders such as lignin, sodium lignin sulfonate and ammonium lignin sulfonate. The synthetic resin binders include polyolefins such as high-density polyethylene, low-density polyethylene and polypropylene, halogenated polyolefins such as polychloroethylene and polypropylene chloride, acrylic polymers such as polyacrylonitrile and polymethylmethacrylate, vinyl polymers such as polystyrene, acrylonitrile-polystyrene-butadiene copolymer, polyvinyl chloride, polyvinyl acetate, vinyl chloride-vinyl acetate copolymer, chlorinated vinyl chloride and polyvinyl ether, synthetic rubbers such as polyvinylidene chloride, ketone-formalin resin, phenoxy resin, polybutadiene, polyisobutylene and polyisoprene, silicon resins, fluorine resins such as polyvinylidene fluoride and polytrifluoroethylene, acetal resins such as polyacetal, polyesters such as polyethylene terephthalate, polyamides such as nylon 6, nylon 66, polyimides, olefin oxides such as polyethylene oxide and polyphenylene oxide, carbonate resins such as polycarbonate, polysulfone resins, polyurethanes such as polyurethane resins and polyurethane urea, epoxy resins, phenol resins, melamine resins, maleic acid resins, urea resins, and polyvinylpyrrolidone, etc.

When the binder is water-soluble, it may be dissolved in water to add as an aqueous solution, added as a powder, melted with heat to use as a melt, or dispersed in water to use as an emulsion.

When the binder is water-insoluble, the binder is preferably dispersed in water to add as an emulsion, melted with heat to use as a melt, or dispersed in water to use as an emulsion.

The binder may be mixed with two or more binders at any ratio to use. In addition, an amount of the binder can be varied depending on its types, but is usually 0.1-40 wt %, preferably 1-30 wt % relative to a total weight of a base material composed of multifilament made of polyester.

The present pest control material can be directly used as a fabric in the net form made by tricot knitting, raschel knitting, and plain knitting, which is formed by retaining the present compound in a base material composed of a multifilament made of polyester according to any process such as immersing, spreading and coating, or can be used as a mosquito bed net formed by sewing the fabric. The mosquito bed net form includes a mosquito bed net formed by sewing the fabric into a square pole or a trapezoidal cone using a fiber-shaped support material inactive to the present compound as needed, and advantageously, any ideas are applied to the mosquito bed net to acquire a shape easy to use depending on the size of the room or the size of the bed. The method of suspending the mosquito bed net may be suspended from the ceiling via a string-shaped support material inactive to the present compound as needed from the ceiling, or may be suspended from the walls using hooks that are driven into the walls. The mosquito bed net is usually used in the manner of covering the room or the bed only during the sleep hours, however, may be used all the day without any problem as long as the mosquito bed net does not make an obstruct. When the pest control material is used as a mosquito bed net, an infectious diseases (such as malaria)-vector mosquito contacts with the present compound present on the surface of the filament, and an insecticidal effect and a blood-sucking inhibiting effect can be thereby exerted. The malaria-vector mosquito is nocturnally active and starts its blood-sucking activity when people fall asleep at night.

Thus, in the case where the mosquito tries to approach a person while seeking a source to suck blood, if the person is asleep in the mosquito bed net, the mosquito touches the mosquito bed net before approaching the person, and as a result, the mosquito is efficiently brought into contact with the present compound. The mosquito tormentedly dies or loses its motivation to suck blood by being brought into contact with the present compound. Also, since the present compound is contained in the filaments by kneading the present compound therein, no more ingredients than a necessary amount is not drifted in the room, and the residual efficacy for a prolonged period can also be expected.

Besides a mosquito bed net, the form of the present pest control material includes, for example, bedclothes, mattress, pillow, quilt, cushion, curtain, wallpaper, carpet material, and net (net door) for window, cupboard, and door. The form further includes geotextile, tent, shoe insole, clothes such as socks, pants, shirt and uniform to be applied to body surface to prevent an insect bite, and horse blankets.

Examples of the pests that can be controlled by the pest control material of the present invention include House mosquitoes (*Culex* spp.) such as common house mosquitoes (*Culex pipiens pallens*), southern house mosquito (*Culex quinquefasciatus*), London underground mosquito (*Culex pipiens* f. *molestus*), and small size common house mosquito (*Culex tritaeniorhynchus*); Mosquito-eating mosquitoes (*Lutzia* spp.) such as *Lutzia vorax* (*Culex halifaxii*); Striped mosquitoes (*Aedes* spp.) such as Asian tiger mosquito (*Aedes albopictus*), yellow fever mosquito (*Aedes aegypti*), Mosquito larva (*Aedes togoi*), *Vexans* mosquito (*Aedes vexans nipponii*), *Ochlerotatus dorsalis* (*Aedes dorsalis*), and *Armigeres subalbatus*; Biting midges (*Ceratopogonidae* spp.) such as *Mansonia uniformis; Tripteroides* spp. such as *Tripteroides bambusa; Anopheles* spp. such as Cancer Vieja Madara mosquito (*Anopheles gambiae*), Chinese *anopheles* (*Anopheles sinensis*), and malaria mosquito (*Anopheles minimus*); Non-biting midges (*Chironomidae* spp.) such as *Chironomus yoshimatsui, chironomus plumosus, Propsilocerus akamusi*, striped chironomid, Oyama Chibi midges (*Tanytarsus*); Horseflies (*Tabanus* spp.); Flies (*Diptera* spp.); Black flies (*Simulium* spp.); Sandflies (*Phlebotominae* spp.); Biting midges (*Ceratopogonidae* spp.); Tsetse flies (*Glossinidae* spp.); Fleas (*Ctenocephalides* spp.); Louces (*Phthiraptera* spp.); Bed bugs (*Cimex lectularius* spp.); Assassin bugs (*Triatoma* spp.); Cockroaches (*blattodea* spp.); Ants (*Formicidae* spp.); Termites (*Isoptera* spp.); Mites (*Acari* spp.); Ixodides (*Ixodes* spp.).

The method for controlling pests of the present invention comprises placing the pest control material of the present invention in habitat of the pests, especially, in the vicinity of an inducing source such as a human being or an animal, and when the pest tries to approach the inducing source, the pest is brought into contact with the pest control material of the present invention, and as a result, an insecticidal effect and a blood-sucking inhibiting effect of the present compound retained on the surface in the pest control material can control the pests. Also a use as a trap of the pest control material in combination with the inducing sources such as a bait, a heat source, and a light source can control the pests.

EXAMPLES

The present invention is described in more detail below with reference to Preparation Examples and Test Examples, but the present invention should not be limited thereto.

First, the Preparation Examples are described below.

Preparation Example 1

To a mixture of 2.00 g (10.57 mmol) of [2-(4-trifluoromethylphenyl)ethylamine and 20 ml of DMF were added 2.92 g (21.13 mmol) of potassium carbonate and 2.06 g (11.63 mmol) of 4,5-dichloro-6-ethylpyrimidine, and the reaction mixture was stirred for 5 hours at 90° C. After cooling to room temperature, 60 ml of water was added thereto, and the mixture was extracted three times with ethyl acetate. The organic layer was washed with water and brine, and dried over anhydrous sodium sulfate, and was then concentrated. The residue was subjected to a silica gel column chromatography to give 5-chloro-4-ethyl-6-[2-(4-trifluoromethylphenyl)ethylamino]pyrimidine (the present compound) 3.00 g.

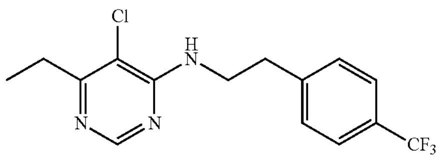 [SMILES: CCc1ncnc(NCCc2ccc(C(F)(F)F)cc2)c1Cl]

$^1$H-NMR ($CDCl_3$) δ: 1.27 (3H, t, J=7.5 Hz), 2.79 (2H, q, J=7.5 Hz), 3.00 (2H, t, J=7.0 Hz), 3.79 (2H, q, J=7.0 Hz), 5.42 (1H, bs), 7.35 (2H, d, J=7.9 Hz), 7.58 (2H, d, J=7.9 Hz), 8.45 (1H, s).

Next, the preparation examples about Textile products A, B, E, F, G, H, and I of the present pest control material, and Textile products C, D, J, and K for comparison are described.

Preparation Example 2

(1) A Process for Preparing Textile Product A

SORPOL1200 (0.053 ml), dimethyl sulfoxide (0.526 ml), and xylene (0.421 ml) were mixed to obtain Mixed solution (A). Further, cyclohexane (0.9 ml) and dimethyl sulfoxide (0.1 ml) were mixed to obtain Mixed solution (B). To screw bottle charged with the present compound (7.8125 mg), Mixed solution (A) (1 ml), Mixed solution (B) (1 ml), and deionized water (18 ml) were added, and was well mixed to obtain Impregnation solvent A. A knitted fabric made of polyester composed of a multifilament having a thickness of 0.2 mm and a hole size of 2 mm was cut out at a length of 25 cm and a width of 25 cm, and spread in a stainless steel pan. Impregnation solvent A was poured into the knitted fabric made of polyester, and the fabric was blended with tweezers to prepare Textile product A. After that, Textile product A was dried under shaded condition at room temperature overnight.

Preparation Example 3

(1) A Process for Preparing Textile Product B

To screw bottle charged with the present compound (15.625 mg), Mixed solution (A) (1 ml) and Mixed solution (B) (1 ml) prepared in the same manners as described in Preparation Example 2, and deionized water (18 ml) were added, and well mixed to obtain Impregnation solvent B. A knitted fabric made of polyester composed of a multifilament having a thickness of 0.2 mm and a hole size of 2 mm was cut out at a length of 25 cm and a width of 25 cm, and spread in a stainless steel pan. Impregnation solvent B was poured into the knitted fabric made of polyester, and the fabric was blended with tweezers to prepare Textile product B. After that, Textile product B was dried under shaded condition at room temperature overnight.

Preparation Example 4

(1) A Process for Preparing Textile Product C

To screw bottle charged with Deltamethrin (15.625 mg), Mixed solution (A) (1 ml) and Mixed solution (B) (1 ml) prepared in the same manners as described in Preparation Example 2, and deionized water (18 ml) were added, and well mixed to obtain Impregnation solvent C. A knitted fabric made of polyester composed of a multifilament having a thickness of 0.2 mm and a hole size of 2 mm was cut out at a length of 25 cm and a width of 25 cm, and spread in a stainless steel pan. Impregnation solvent C was poured into the knitted fabric made of polyester, and the fabric was blended with tweezers to prepare Textile product C. After that, Textile product C was dried under shaded condition at room temperature overnight.

Preparation Example 5

(1) A Process for Preparing Textile Product D

Mixed solution (A) (1 ml) and Mixed solution (B) (1 ml) prepared in the same manners as described in Preparation Example 2, and deionized water (18 ml) were added and well mixed to obtain Impregnation solvent D. A knitted fabric made of polyester composed of a multifilament having a thickness of 0.2 mm and a hole size of 2 mm was cut out at a length of 25 cm and a width of 25 cm, and spread in a stainless steel pan. Impregnation solvent D was poured into the knitted fabric made of polyester, and the fabric was blended with tweezers to prepare Textile product D. After that, Textile product D was dried under shaded condition at room temperature overnight.

Preparation Example 6

(1) A Process for Preparing Textile Product E

To a 200 ml measuring flask charged with the present compound (2.291 g), ethanol was added and dissolved to make 200 ml of Chemical (C). To a 100 ml measuring flask charged with acrylic acid ester copolymer emulsion (44%, 18.940 g), ethanol was added and dispersed to make 100 ml of Binder solution E. To a 100 ml measuring flask charged with Chemical (C) (10 ml) and Binder solution E (25 mL), ethanol was added to make 100 ml of Impregnation solvent E. A knitted fabric made of polyester composed of a multifilament having a thickness of 0.2 mm and a hole size of 2 mm was cut out at a length of 25 cm and a width of 25 cm, and spread in a stainless steel pan. Impregnation solvent E was poured into the knitted fabric made of polyester, and the fabric was blended with tweezers to prepare Textile product E. After that, Textile product E was dried under shaded condition at room temperature overnight.

Preparation Example 7

(1) A Process for Preparing Textile Product F

To a 100 ml measuring flask charged with polycarbonate urethane emulsion (40%, 20.730 g), ethanol was added and dispersed to make 100 ml of Binder solution F. To a 100 ml measuring flask charged with Chemical (C) (10 ml) prepared in Preparation Example 6 and Binder solution F (25 mL), ethanol was added to make 100 ml of Impregnation solvent F. A knitted fabric made of polyester composed of a multifilament having a thickness of 0.2 mm and a hole size of 2 mm was cut out at a length of 25 cm and a width of 25 cm, and spread in a stainless steel pan. Impregnation solvent F was poured into the knitted fabric made of polyester, and the fabric was blended with tweezers to prepare Textile product F. After that, Textile product F was dried under shaded condition at room temperature overnight.

Preparation Example 8

(1) A Process for Preparing Textile Product G

To a 100 ml measuring flask charged with acrylic acid ester copolymer emulsion (44%, 18.940 g), ethanol was added and dispersed to make 100 ml of Binder solution G. To a 100 ml measuring flask charged with Chemical (C) (14.5 ml) prepared in Preparation Example 6 and Binder solution G (25 mL), ethanol was added to make 100 ml of Impregnation solvent G. A knitted fabric made of polyester composed of a multifilament having a thickness of 0.2 mm and a hole size of 2 mm was cut out at a length of 25 cm and a width of 25 cm, and spread in a stainless steel pan. Impregnation solvent G was poured into the knitted fabric made of polyester, and the fabric was blended with tweezers to prepare Textile product G. After that, Textile product G was dried under shaded condition at room temperature overnight.

Preparation Example 9

(1) A Process for Preparing Textile Product H

To a 100 ml measuring flask charged with polycarbonate urethane emulsion (40%, 20.730 g), ethanol was added and dispersed to make 100 ml of Binder solution H. To a 100 ml measuring flask charged with Chemical (C) (14.5 ml) prepared in Preparation Example 6 and Binder solution H (25 mL), ethanol was added to make 100 ml of Impregnation solvent H. A knitted fabric made of polyester composed of a multifilament having a thickness of 0.2 mm and a hole size of 2 mm was cut out at a length of 25 cm and a width of 25 cm, and spread in a stainless steel pan. Impregnation solvent H was poured into the knitted fabric made of polyester, and the fabric was blended with tweezers to prepare Textile product H. After that, Textile product H was dried under shaded condition at room temperature overnight.

Preparation Example 10

(1) A Process for Preparing Textile Product I

To a 100 ml measuring flask charged with polycarbonate urethane emulsion (40%, 20.730 g), ethanol was added and dispersed to make 100 ml of Binder solution I. To a 100 ml measuring flask charged with Chemical (C) (45.5 ml) prepared in Preparation Example 6 and Binder solution I (25 mL), ethanol was added to make 100 ml of Impregnation solvent I. A knitted fabric made of polyester composed of a multifilament having a thickness of 0.2 mm and a hole size of 2 mm was cut out at a length of 25 cm and a width of 25 cm, and spread in a stainless steel pan. Impregnation solvent I was poured into the knitted fabric made of polyester, and the fabric was blended with tweezers to prepare Textile product I. After that, Textile product I was dried under shaded condition at room temperature overnight.

Preparation Example 11

(1) A Process for Preparing Textile Product J

To a 200 ml measuring flask charged with Deltamethrin (2.291 g), ethanol was added and dissolved to make 200 ml of Chemical (D). To a 100 ml measuring flask charged with acrylic acid ester copolymer emulsion (44%, 18.940 g), ethanol was added and dispersed to make 100 ml of Binder solution J. To a 100 ml measuring flask charged with Chemical (D) (14.5 ml) and Binder solution J (25 mL), ethanol was added to make 100 ml of Impregnation solvent J. A knitted fabric made of polyester composed of a multifilament having a thickness of 0.2 mm and a hole size of 2 mm was cut out at a length of 25 cm and a width of 25 cm, and spread in a stainless steel pan. Impregnation solvent J was poured into the knitted fabric made of polyester, and the fabric was blended with tweezers to prepare Textile product J. After that, Textile product J was dried under shaded condition at room temperature overnight.

Preparation Example 12

(1) A Process for Preparing Textile Product K

To a 100 ml measuring flask charged with acrylic acid ester copolymer emulsion (44%, 18.940 g), ethanol was added and dispersed to make 100 ml of Binder solution K. To a 100 ml measuring flask charged with Binder solution K (25 ml), ethanol was added to make 100 ml of Impregnation solvent K. A knitted fabric made of polyester composed of a multifilament having a thickness of 0.2 mm and a hole size of 2 mm was cut out at a length of 25 cm and a width of 25 cm, and spread in a stainless steel pan. Impregnation solvent K was poured into the knitted fabric made of polyester, and the fabric was blended with tweezers to prepare Textile product K. After that, Textile product K was dried under shaded condition at room temperature overnight.

Second, the Test Examples are described below.

Test Example 1

The basic insecticidal activity of the present compound was examined using a topical application method. Various concentrations of acetone solutions of the present compound were previously prepared. A female adult of Cancer Vieja Madara mosquito (*Anopheles gambiae* Kisumu-strain) was treated by dropping via a micro syringe 0.3 μL of the prepared acetone solution to a thoracodorsal region of the mosquito under anesthesia with carbon dioxide gas that did not yet suck any blood. After the treatment, the female adults of Cancer Vieja Madara mosquito were moved into a plastic cup (having a diameter of 9 cm and a height of about 4.5 cm), and was fed with 5% sugar water. The mortality after 24 hours was examined. The number of the tested female adults of Cancer Vieja Madara mosquito was 10 heads per each one concentration in two replicate experiments. The 50% lethal dose (the $LD_{50}$ value) of the present compound was calculated from the test result using probit method. The same experiment was conducted using Deltamethrin as a control. The lower 50% lethal dose of a compound means the higher basic insecticidal activity of the compound. The ratio of the $LD_{50}$ value of the present compound relative to the $LD_{50}$ value of Deltamethrin was calculated to acquire the relative efficacy of the present compound to Deltamethrin. The result thereof is shown in Table 1.

TABLE 1

| Tested Compound | 50% Lethal Dose ($LD_{50}$) (μg/female) | Relative Efficacy |
|---|---|---|
| The present compound | 0.009400 | 0.0100 |
| Deltamethrin | 0.000094 | 1 |

Test Example 2

The lethal effect of Textile products A to D obtained in Preparation Examples 2 to 5 on a female adult of Cancer Vieja Madara mosquito (*Anopheles gambiae* Kisumu-strain)) was examined according to a standard WHO tunnel method described in the below-mentioned reference. The device used for the standard WHO tunnel method was assembled according to the description in the below-mentioned reference. Specifically, the device was consisted of a glass tunnel portion (having a height of 25 cm, a width of cm, and a length of 60 cm) and cage portions (each having 25-cm sides) connected to both ends of the tunnel portion. Each of the textile products was fixed to a metal frame, and an area of 20 cm×20 cm was exposed, and was placed at a position that was ⅓ from an end of the glass tunnel (namely, 20 cm from the end) to dispose two sections in the tunnel. Nine (9) holes each having a diameter of 1 cm were disposed at 9 points at intervals of 5 cm in each of the textile products for the mosquitoes to pass therethrough. When the mosquitoes passed through these holes to move between the sections, the mosquitoes necessarily brought into contact with the textile product. An inducing source was placed in a short section of the tunnel, and at 18:00, 110 heads of the female adults of Cancer Vieja Madara mosquito (*Anopheles gambiae* Kisumu-strain) each at 3 to 5 days instar larval after an adult eclosion were released in the section that is opposite to the inducing source and is across the tested sample.

After the test came to an end at 9:00 in the next morning, the female adults of Cancer Vieja Madara mosquito were moved into a plastic cup (having a diameter of 9 cm and a height of about 4.5 cm), and provided with sugar water (5%). After 24 hours, the number of the dead insects was counted to calculate the mortality based on Equation (a). The corrected mortality of the tested sample was calculated based on Equation (b) which corrects a mortality of the tested sample using a mortality of the control sample. A sample having a higher corrected mortality after 24 hours indicates a higher contact insecticidal activity under the presence of an attracting source. Textile product D was used as a control. The result is shown in Table 2.

REFERENCE

WHOPES (2005), Guidelines for laboratory and field testing of long-lasting insecticidal mosquito bed nets, WHO/CDS/WHOPES/GCDPP/2005.11 Geneva, WHO.

Mortality of Insects after 24 hours (%)=Number of Dead Insects after 24 hours/Total Number of tested Insects×100 Eq. (a)

Corrected Mortality (%)=((Mortality of tested samples (%)−Mortality of control samples (%))/(100−Mortality of control samples (%)))×100 Eq. (b)

TABLE 2

| Samples | Corrected Mortality after 24 hours (%) |
|---|---|
| Textile product A | 95.7 |
| Textile product B | 96.8 |
| Textile product C | 91.3 |

Test Example 3

The basic insecticidal activity of each of the present compound and Deltamethrin was examined using the same method as that used in Test Example 1. Here the tested female adults of Cancer Vieja Madara mosquito were pyrethroid-resistive female adults of Cancer Vieja Madara mosquito (*Anopheles gambiae* VK7-strain), and the number of the tested insects was 10 heads per each one concentration in two replicate experiments. The ratio of the $LD_{50}$ value of the present compound relative to the $LD_{50}$ value of Deltamethrin was calculated to acquire the relative efficacy of the present compound to Deltamethrin. The result thereof is shown in Table 3.

TABLE 3

| Tested Compound | 50% Lethal Dose ($LD_{50}$) (μg/female) | Relative Efficacy |
|---|---|---|
| The present compound | 0.01833 | 0.05674 |
| Deltamethrin | 0.00104 | 1 |

Test Example 4

The lethal effect of Textile products A to D obtained in Preparation Examples 2 to 5 on pyrethroid-resistive Cancer Vieja Madara mosquito (*Anopheles gambiae* VK7-strain) was examined using the same method as that used in Test Example 2 except that pyrethroid-resistant Cancer Vieja Madara mosquito (*Anopheles gambiae* VK7-strain) was used instead of adult female Cancer Vieja Madara mosquito (*Anopheles gambiae* Kisumu-strain). Textile product D was used as a control. The result is shown in Table 4.

TABLE 4

| Samples | Corrected Mortality after 24 hours (%) |
|---|---|
| Textile product A | 72.2 |
| Textile product B | 93.1 |
| Textile product C | 29.2 |

Test Example 5

The blood sucking inhibiting effect of Textile products E to K obtained in Preparation Examples 6 to 12 on the pyrethroid-resistive female adults of Cancer Vieja Madara mosquito (*Anopheles gambiae* VK7-strain) was examined according to a standard WHO tunnel method described in the below-mentioned reference. The device used for the standard WHO tunnel method was assembled according to the description in the below-mentioned reference. Specifically, the device was consisted of a glass tunnel portion (having a height of 25 cm, a width of 25 cm, and a length of 60 cm) and cage portions (each having 25-cm sides) connected to both ends of the tunnel portion. Each of the textile products was fixed to a metal frame, and an area of 20 cm×20 cm was exposed, and was placed at a position that was ⅓ from an end of the glass tunnel (namely, 20 cm from the end) to dispose two sections in the tunnel. Nine (9) holes each having a diameter of 1 cm were disposed at 9 points at intervals of 5 cm in each of the textile products for the mosquitoes to pass therethrough. When the mosquitoes passed through these holes to move between the sections, the mosquitoes necessarily brought into contact with the textile product. An inducing source was placed in a short section of the tunnel, and at 18:00, 110 heads of the pyrethroid-resistive female adults of Cancer Vieja Madara mosquito (*Anopheles gambiae* VK7-strain) each at 3 to 5 days instar larval after an adult eclosion were released in the section that is opposite to the inducing source and is across the tested sample.

After the test came to an end at 9:00 in the next morning, the female adults of Cancer Vieja Madara mosquito were moved into a plastic cup (having a diameter of 9 cm and a height of about 4.5 cm), and the number of blood-sucked insects was counted to acquire the blood-sucking rate according to Eq. (c). The blood-sucking inhibiting rate for the tested sample was calculated according to Eq. (d) that corrects using the blood-sucking rate of the control sample. A sample with a higher blood-sucking inhibiting rate means a higher blood-sucking inhibiting activity of the sample under the condition of the presence of the inducing source. The control sample was Textile product K. The result is shown in Table 5.

REFERENCE

WHOPES (2005), Guidelines for laboratory and field testing of long-lasting insecticidal mosquito bed nets, WHO/CDS/WHOPES/GCDPP/2005.11 Geneva, WHO.

Blood-Sucking Rate (%)=Number of Blood-Sucking Insects/Total Number of tested Insects×100 Eq. (c)

Blood-Sucking inhibiting Rate (%)=(Blood-Sucking Rate of control samples (%)−Blood-Sucking Rate of tested samples (%))/Blood-Sucking Rate of control samples (%)×100 Eq. (d)

TABLE 5

| Samples | (%) |
|---|---|
| Textile product E | 94.3 |
| Textile product F | 100 |
| Textile product G | 100 |
| Textile product H | 97.0 |
| Textile product I | 100 |
| Textile product J | 37.4 |

The invention claimed is:

1. A pest control material which is formed by retaining 5-chloro-4-ethyl-6-[2-(4-trifluoromethylphenyl)ethylamino]pyrimidine on a surface of a base material composed of a multifilament made of polyester.

2. The pest control material according to claim 1, wherein the material is in a net form.

3. The pest control material according to claim 1, wherein the material is in a mosquito bed net form.

4. The pest control material according to claim 1, wherein the content of 5-chloro-4-ethyl-6-[2-(4-trifluoromethylphenyl)ethylamino]pyrimidine is 0.1 to 10% by mass relative to a total amount of the pest control material.

5. The pest control material according to claim 1, which is further equipped with an inactive support material.

6. A method for controlling pests comprising placing the pest control material according to claim 1, in habitat of the pests.

* * * * *